(12) United States Patent
Wester et al.

(10) Patent No.: US 8,575,100 B2
(45) Date of Patent: *Nov. 5, 2013

(54) TC AND RE LABELED RADIOACTIVE GLYCOSYLATED OCTREOTIDE DERIVATIVES

(75) Inventors: Hans-Jurgen Wester, Illmmuenster (DE); Margret Schottelius, Munich (DE); Markus Schwaiger, Munich (DE)

(73) Assignee: Mallinckrodt LLC, Hazelwood, MO (US)

( * ) Notice: Subject to any disclaimer, the term of this patent is extended or adjusted under 35 U.S.C. 154(b) by 315 days.

This patent is subject to a terminal disclaimer.

(21) Appl. No.: 12/556,698

(22) Filed: Sep. 10, 2009

(65) Prior Publication Data

US 2009/0324497 A1    Dec. 31, 2009

Related U.S. Application Data

(63) Continuation of application No. 10/475,696, filed as application No. PCT/US02/12565 on Apr. 23, 2002, now Pat. No. 7,589,061.

(30) Foreign Application Priority Data

Apr. 23, 2001    (EP) ..................... 01201466

(51) Int. Cl.
*A61K 38/31*    (2006.01)
*A61P 5/06*    (2006.01)

(52) U.S. Cl.
USPC ........................................ 514/11.1

(58) Field of Classification Search
None
See application file for complete search history.

(56) References Cited

U.S. PATENT DOCUMENTS 5,656,721 A    8/1997    Albert et al.
5,753,206 A *  5/1998    McBride et al. ............. 424/1.69

FOREIGN PATENT DOCUMENTS

| JP | 1 95737 | 4/1989 |
| JP | 10259197 A | 9/1998 |
| JP | 10512852 | 12/1998 |
| JP | 2000506854 | 6/2000 |
| JP | 2001500116 A | 1/2001 |
| WO | 9617618 A1 | 6/1996 |
| WO | 9739021 A1 | 10/1997 |
| WO | 9804294 A2 | 2/1998 |
| WO | 9958162 A1 | 11/1999 |
| WO | 0053790 A1 | 9/2000 |

OTHER PUBLICATIONS

Alberto et al., "A Novel Organometallic Aqua complex of Technetium for the Labeling of Biomolecules . . . " J. Am. Chem.. Soc., 1998, 120, pp. 7987-7988.

(Continued)

*Primary Examiner* — Thomas Heard

(57) ABSTRACT

Improved sst-receptor binding peptidic ligands for diagnostic and therapeutic applications in nuclear medicine are provided. The improved ligands contain either natural or unnatural amino acids or peptidomimetic structures that are modified at either the N-terminal or the C-terminal end or at both termini, a carbohydrate unit and a chelator or prosthetic group to provide a complexation of a radioisotope binding or holding the radioisotope. The sst- or SSTR-receptor binding peptidic ligands may also contain one or more multifunctional linker units optionally coupling the peptide, and/or the sugar moiety and/or the chelator and/or the prosthetic group. Upon administering the ligand to a mammal through the blood system the ligand provides improved availability, clearance kinetics, sst-receptor targeting and internalization over the non-carbohydrated ligands.

8 Claims, 3 Drawing Sheets

(56) References Cited

OTHER PUBLICATIONS

Banguard et al., "Detection of somatostatin receptor-positive tumours using the new $^{99m}$Tc-tricine-HYNIC-D_Phe$^1$-Tyr$^3$-octreotide: first results in patients and comparison with $^{111}$In-DTPA-d-Phe$^1$-octreotide", European Journal of Nuclear Medicine, Jun. 2000, vol. 27, No. 6, pp. 628-637.

Connors et al., "Biotransformation of a somatostatin analogue in precision-cut liver and kidnew slices from rat, dog and man", Xenobiotica, 1996, 26(2), pp. 133-141.

Cox et al., "Catecholate LMCT Bands as Probes for the Active Sites of Nonheme Iron Oxygenases", J. Am. Chem. Soc., 1988, 110, pp. 2026-2032, and supporting material.

Egli et al., "Oranometallic 99mTc-Aquaion Labels Peptide to an Unprecedented High Specific Activity", Journal of Nuclear Medicine, 40(11), 1999, pp. 1913-1917.

Fricker et al., "Intestinal Absorption of Sugar-Coupled Somatostatin Analogs", Journal of Pharmaceutical Sciences, Nov. 1996, vol. 85, No. 11, pp. 1211-1214.

Wester et al., "99MTC (CO)3-Labeled Carbohydrated SSTR-LIGANDS: Synthesis Internalization . . . ", Journal of Nuclear Medicine, 42(5), Suppl., 2001, p. 115, XP 001149171.

Lewis et al., "Comparison of Four 64Cu-Labeled Somatostatin analogues in Vitro and in a Tumor Bearing Rat Model . . . ", J. Med. Chem., 1999, 42, pp. 1341-1347.

Messer, "Vasopressin and Oxytocin" [online], Apr. 3, 2000 [retrieved on Dec. 19, 2006]. Retrieved from the internet: <URL:http://www.neurosci.pharm.utoledo.edu/MBC3320/vasopressin.htm>.

Schottelius et al., "Improvement of Pharmacokinetics of Radioinated Tyr3-Octreotide by Conjugation with Carbohydrates", 2002, Bioconjugate Chemistry, 13, pp. 1021-1030.

Fricker et al., "Heterogeneity in Hepatic Transport of Somatostatin Analog Octapeptides", Hepatology, Jul. 1994, pp. 191-200.

Marmion, et al., Journal of Nuclear Medicine, Suppl. 40P, 2000, Scientific Abstracts of the 47th Annual Meeting of the Society of Nuclear Medicine, Abstract No. 156.

Schottelius, et al., Journal of Nuclear Medicine, Suppl. 40P, 2000, Scientific Abstracts of the 47th Annual Meeting of the Society of Nuclear Medicine, Abstract No. 157.

Albert, et al., "SDZ CO 611: a highly potent glycated analog of Somatostatin with improved oral activity," Life Sciences, 1993, 53(6), pp. 517-525, XP 008018715.

Du, et al., "Technetium-99m labeling of glycosylated Somatostatin-14," Applied Radiation and Isotopes, 2001, vol. 55, pp. 181-1B7, XP002247184.

Wester, et al., "Glycation of SST-Receptor-Agonists: Improvement of Dynamic Ligand Trafficking . . . ," J. Label. Compd. Radiopharmaceuticals, 2001, 44, Suppl. 1, pp. S93-S95, XP 008018713.

* cited by examiner

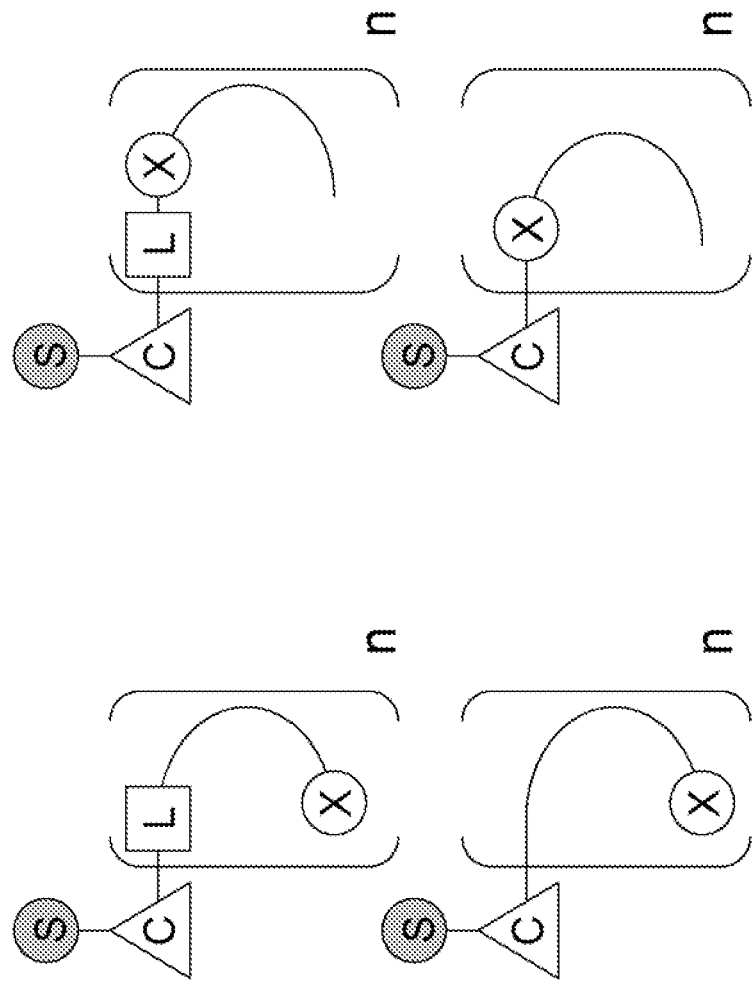

TC AND RE LABELED RADIOACTIVE GLYCOSYLATED OCTREOTIDE DERIVATIVES

CROSS REFERENCE TO RELATED APPLICATIONS

This application is a continuation of prior U.S. patent application Ser. No. 10/475,696, filed May 14, 2004, which is a national stage application of PCT/US02/12565, filed Apr. 23, 2002, which claims the benefit of European Application No. 01201466.8, filed Apr. 23, 2001.

SUMMARY OF THE INVENTION

The present invention relates to novel radioactive octreotide derivatives that are glycosylated and bind the somatostatin receptor.

These so-called SSTR-ligands are suitable for the in vivo targeting of somatostatin receptors and find broad application in nuclear medicine.

Essential parts of these molecules are sugar moieties conjugated directly or via linkers to the bioactive part of the molecule. Compared to the corresponding non-carbohydrated derivatives, these derivatives, labeled with radioisotopes such as Rhenium and Technetium, either via direct reductive methods or via tricarbonyl complexes, lead to potent somatostatin receptor ligands with improved tumor/non-tumor accumulation ratios, improved pharmacokinetics and improved internalization kinetics.

The somatostatin receptor binding peptidic ligand of this invention are prepared from natural or unnatural (prepared) ligands. These ligands bear structural modifications at the N-terminal end or the C-terminal end or both termini. Said peptide ligands have affinity to sst-receptors and are graphically represented by the structure:

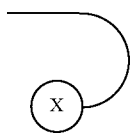

wherein X indicates the C-terminus of the ligand. In the compositions of this invention wherein there may be multiple ligands there is permitted the formation of di- and multimers by mixed C- and N-terminal coupling of the peptide chain. Thus, the scope of this invention covers homo-, dimer, homomultimers or different receptor binding structures, heterodimers, and heteromultimers. The di- and multimers can be formed by mixed C- and N-terminal coupling of the peptide chain.

The ligand composition of this invention optionally contains at least one linker unit that can be multifunctional. Such linker unit allows coupling together of the peptide, sugar moiety and chelator via a condensation, acylation, alkylation, substitution or addition reaction. Typical linker units comprise ligands taken from peptidic or other organic structures such as L- or D-amino acids such as lysine, ornithine serine, glutamic acid, aspartic acid, O-amine serine, mercaptopropionic acid, hydroxy carbonic acids, amino carbonic acids, halogen carbonic acids or polyamino acids.

The improved somatostatin receptor binding peptidic ligand of this invention comprises a carbohydrate, specifically a sugar such as a mono-, di- and trisaccharide. Typical suitable sugars include glucose, galactose, maltose, mannose, maltrotriose and lactose coupled via covalent linkage. That is, the sugar can be combined via the Maillard reaction and Amadori rearrangement, glycosidic linkage, alklation, allyation or coupled via complex formation after modification, that is, formation of carbohydrate isonitriles or carbohydrated phosphates.

Another component of the improved somatostatin receptor binding peptidic ligand of this invention is a chelator. Typical chelators are peptidic or non-peptidic structures suitable for mono- or multidentate complexation of radioisotopes of Tc and Re. The chelator useful in compositions of this invention comprise one or more (ligand and coligand(s)) organic molecules containing any number of functional groups necessary to the complexation of the radiometals, depending on its oxidation state and complex geometry. Exemplary suitable chelators are, for example, histidine, picolylamine diacetic acid, hydroxy nicotine amide (HYNIC), mercaptoacetyl-glycyl-glycyl-glycine (MAG3) and tetrapeptides.

BRIEF DESCRIPTION OF DRAWINGS

To more clearly describe the improved somatostatin receptor binding peptidic ligand of this invention, reference is made to FIGS. 1A-1C. In FIG. 1A-1C there is shown, in graphical schematic form, the various configurations into which the peptide ligands of this invention can be prepared. Other practical configurations may occur to those skilled in this art in keeping with the teaching of this specification.

In FIG. 1A, FIG. 1B and FIG. 1C there is shown mono- di- and multimers (wherein n is an integer of 2 or more) containing a linker moiety, L, sugar moiety, S, and a chelator, C, capable of holding a radioisotope of Tc and Re.

In FIGS. 1A, 1B and 1C the termini of the peptide is designated by indicating the C-terminus by X, the opposite terminus being the N terminus. Thus the pharmacophoric peptide is coupled with the C- or N-terminal end to the linker, chelator, etc. As indicated above, both the peptide ligand and the linker (multifunctional) can comprise natural or unnatural amino acids. Of course, the ligand (i.e. octreotide) will not be employed as the linker in compositions of this invention.

In FIG. 1A there is shown various configurations of compositions of this invention providing multimers of peptide ligands of two or more. The multimers may comprise either identical receptor peptide binding structures (homodimers, homomultimers) or different receptor binding structures (heterodimers, heteromultimers).

In FIG. 1B, there is shown various configurations of monomers some of which contain a linker unit (multifunctional) and four of which do not contain a linker unit. Thus it is seen that a multifunctional linker unit is optional in the compositions of this invention.

In FIG. 1C, there is shown dimers and multimers wherein multiple linker units are employed with varying orientation of the peptide and, of course, multiple peptide ligands.

Figure 1A:
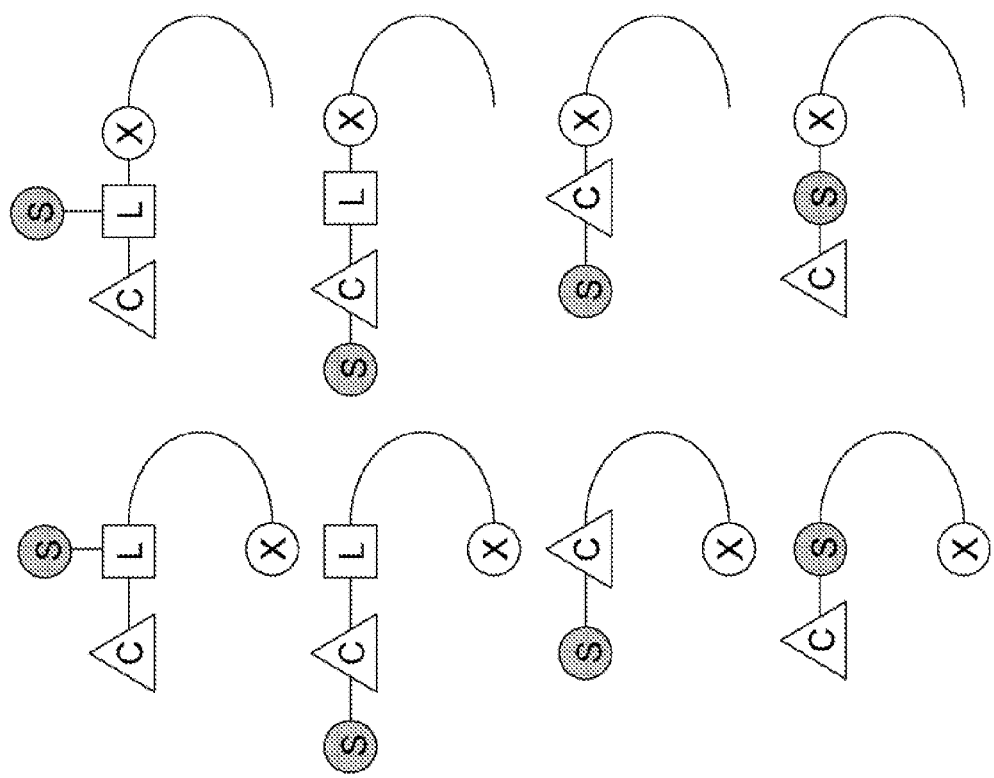
Figure 1B:
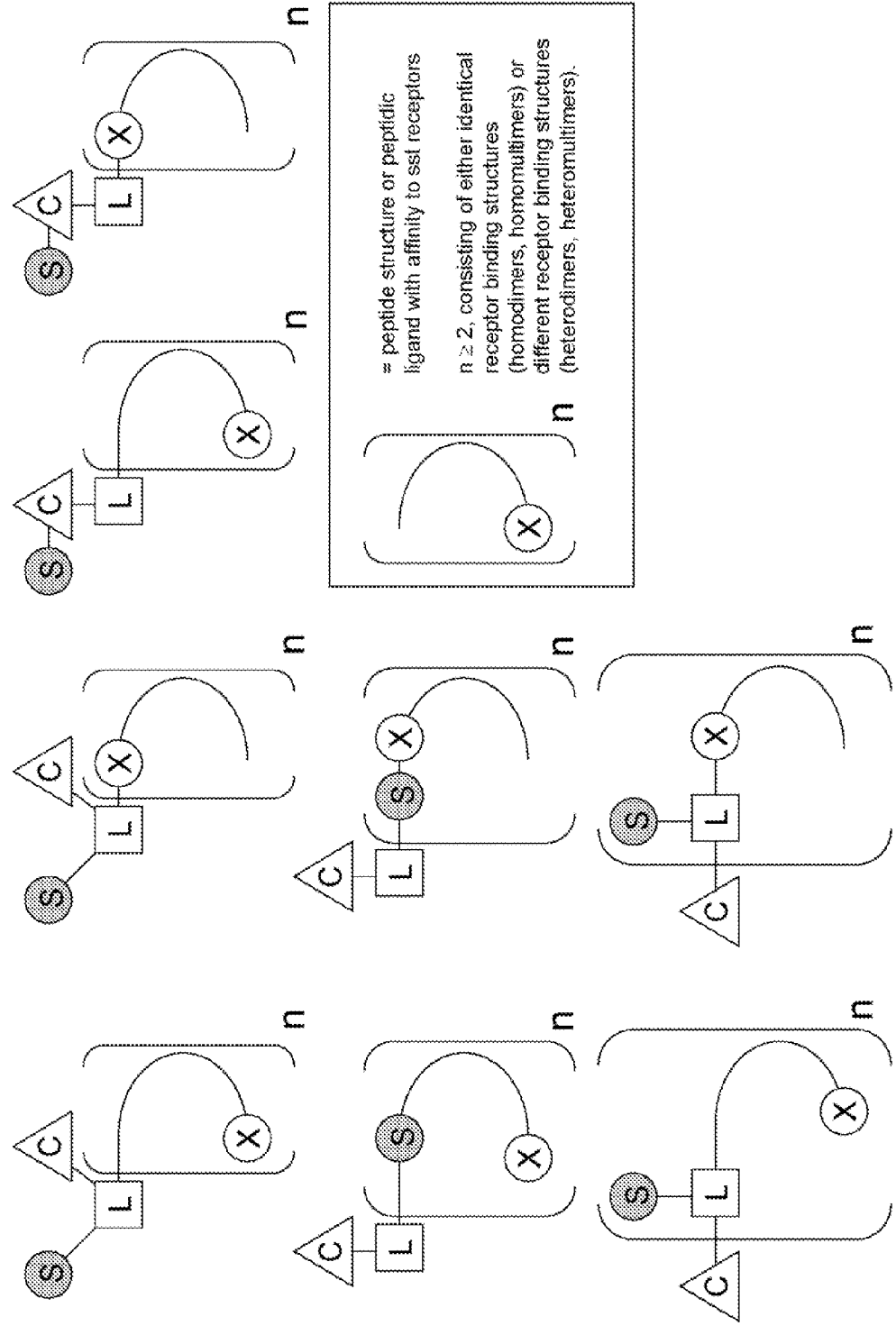

The dimers and multimers shown in FIGS. 1A and 1C can be formed via covalent linkage of the linker or the peptide ligand to the chelator or formation of a complex between the linker and the chelator.

The invention is described in is illustrated in the non-limiting examples that follow.

DETAILED DESCRIPTION

Examples

Example 1

Rational Design of Peptide Radiopharmaceuticals: in Vitro Studies Demonstrate a Synergistic Effect of Carbohydration and C-Terminal Oxidation of Octreotide on Ligand Induced $SST_2$ Internalization Aims:

Besides by its pharmacokinetics, the suitability of a receptor based tracer for imaging and therapeutic purposes is mainly determined by its pharmacodynamic profile. Aim of this study was to investigate the effect of carbohydration of octreotide and octreotate on SSTR endo- and exocytosis (internalization and externalization) and reendocytosis (recirculation).

Methods:

Internalization, externalization and recycling of $[^{125}I]Tyr^3$-octreotide (TOC), $[^{125}I]Tyr^3$-octreotate (TOCA) and their Glucose (Gluc) and Maltotriose (Mtr) derivatives were studied using confluent monolayers of AR42J-cells ($SSTR_2$). The cells were incubated with the radioligand for up to 120 min (n=3). At each time point the activity in the supernatant, the surface-bound and the internalized activity were determined and normalized to the values of TOC. Externalization and recycling was studied after an incubation time of 120 min over 2 h. Specificity of ligand binding was studied in a competition experiment with 10 M Sandostatin.

Results:

After 2 h of incubation the amount of internalized ligand [% internalized TOC] was as follows: Mtr-TOC (35±4%) <Gluc-TOC (121%)<TOCA (154%)<Mtr-TOCA (549%) <Gluc-TOCA (637%). In the competition experiment internalization of all compounds dropped to <0.1±0.02% (30 min) of the applied radioactivity. In the externalization experiment that allowed recycling of the ligands, TOCA and glycated TOCA's showed about ⅔ of extracellularly located radioactivity compared to the experiment without recycling, while about 80% were found for TOC, Gluc-TOC and Mtr-TOC. Carbohydration of TOC had no significant effect on the availability of the ligands on the cell surface, whereas surface concentration of TOCA and Mtr-TOCA is increased by a factor of 2.1 and 2.3 respectively compared to TOC. Gluc-TOCA shows a fivefold increase of the availability of the tracer on the cell surface compared to TOC. The internalization rate (internalized/surface bound act.) of TOC is not significantly affected by glycosylation, whereas TOCA shows a 1.4 fold increase. For Gluc-TOCA and Mtr-TOCA we observed internalization rates of 186 and 171% compared to TOC.

Conclusion:

Using AR42J-cells, carbohydration of TOCA led to a significant increase in cell surface concentration and internalization rate of the radioligands.

Example 2

Carbohydrated Tc-99M-Octreotide Derivatives for SPECT Synthesis, Radiolabelling and In Vivo Data Over the past decade different approaches to $^{99m}$Tc- and $^{18}$F-labelled octreotide derivatives for SSTR-scintigraphy using SPECT and PET have been investigated. Decristoforo et al. showed that $^{99m}$Tc-labelled HYNIC-$Tyr^3$-octreotide with EDDA as a coligand has favourable biokinetics and high tumor uptake in mice.

2-$[^{18}F]$fluoropropionyl-D-$Phe^1$-octreotide, the only $^{18}$F-labelled octreotide analog known so far, shows predominant hepatobiliary excretion, which is one drawback with respect to its application for in vivo SSTR-imaging.

The inventors found that N-terminal glycosylation of radioiodinated $Tyr^3$-octreotide (TOC) and its $Thr^8$-derivative $Tyr^3$-octreotate (TOCA) leads to a significant improvement of the biodistribution, i.e. to an increased tumor accumulation. To investigate the general applicability of this principle, we synthesized and evaluated glycosylated octreotide- and octreotate-derivatives for $^{99m}$Tc-labelling, $N^\alpha$-glycosylated derivatives of $Lys^0(N^\epsilon$-His)-TOC ($K^0$(H)TOC) were used as precursors for $^{99m}$Tc-labelling using the organometallic aquaion $[^{99m}Tc(H_2O)_3(CO)_3]^+$-approach (Egli A. et al. *J. Nucl. Med.* 40: 1913-1917 (1999)). The peptide was synthesized according to a standard Fmoc-SPPS protocol. Conjugation with glucose (Gluc) and maltotriose (Mtr) was performed via Amadori reaction.

$^{99m}$Tc-labelling of the $Lys^5$-deprotected peptides yielded $[^{99m}Tc]$Gluc-$K^0$(H)TOC and $[^{99m}Tc]$Mtr-$K^0$(H)TOC with radiochemical yields >97% based on the aquaion.

Biodistribution studies of the $^{99m}$Tc-labelled derivatives (30 and 120 min p.i.) were performed in AR42J-tumor bearing nude mice (n=3-4). Internalisation and externalisation experiments were carried out using the same cell line.

An increase of internalisation was found for $[^{99m}Tc]$Gluc-$K^0$(H)TOC by a factor of 2.3±0.8 and for $[^{99m}Tc]$Mtr-$K^0$(H)TOC by a factor of 3.6±0.4 compared to the reference $[^{125}I]$TOC. While $[^{125}I]$TOC is rapidly externalised from the cell upon incubation, $[^{99m}Tc]$Gluc-$K^0$(H)TOC remains trapped within the cell up to 120 min. The biodistribution of $[^{99m}Tc]$Gluc-$K^0$(H)TOC and $[^{99m}Tc]$Mtr-$K^0$(H)TOC 2 h p.i. are shown in Table 1.

TABLE 1

Tissue accumulation [% iD/g] of $[^{99m}Tc]$Gluc-$K^0$(H)TOC and $[^{99m}Tc]$Mtr-$K^0$(H)TOC in AR42J tumor bearing nude mice 2 h p.i. (n = 3-4)

|  | $[^{99m}Tc]$Gluc-$K^0$(H)TOC | $[^{99m}Tc]$Mtr-$K^0$(H)TOC |
|---|---|---|
| blood | 1.49 ± 0.18 | 4.12 ± 0.87 |
| liver | 15.89 ± 2.70 | 14.34 ± 1.55 |
| intestine | 2.83 ± 0.28 | 2.02 ± 0.41 |
| stomach | 11.28 ± 2.74 | 6.22 ± 0.75 |
| kidney | 19.49 ± 2.22 | 17.97 ± 2.76 |
| muscle | 0.22 ± 0.04 | 0.40 ± 0.10 |
| adrenals | 6.47 ± 1.46 | 4.94 ± 0.38 |
| pancreas | 6.43 ± 2.09 | 3.32 ± 0.38 |
| tumor | 12.21 ± 0.96 | 14.02 ± 6.33 |

Both glycosylated compounds show high accumulation in $sst_2$ positive tissue 120 min p.i. We suppose that the comparatively high non-specific uptake in excretion organs as well as a delayed blood clearance are due to the insufficient complexation of the $^{99m}$Tc-core by the bidentate histidine ligand. The remaining metal coordination site may be saturated by thiol-containing native proteins in vivo, which can result in rapid trapping of these complexes in the blood, the liver and other excretion organs. The formation of saturated complexes of the $[^{99m}Tc(H_2O))_3(CO)_3]^+$-aquaion with tridentate ligands such as N—Ac-His result in a significant decrease of activity accumulation in non-tumor tissue.

It can be concluded that the introduced tracer design based on the combination of carbohydrate conjugation of octreotide (-tate) and of tridentate complexation of the $[^{99m}Tc(H_2O)_3(CO)_3]^+$-aquaion is the basis of a new series of very promising SSTR-tracers.

Example 3

Glycation of Sst-Receptor-Agonists: Improvement of Dynamic Ligand Trafficking of Radiolabelled Somatostatin Agonists Carbohydration is now found to be a powerful tool to improve the pharmacokinetics of radiolabelled octreotide and $Tyr^3$ analogs. Glycation of octreotide and octreotate significantly reduces hepatobiliary excretion and kidney uptake and enhances tumor uptake and tumor/tissue ratios. Tumor accumulation of a radiolabelled $sst_2$-agonist relies upon the dynamic processes of receptor mediated internalisation, degradation and subsequent intracellular accumulation or recycling of both ligand and/or metabolite. Quantitative analysis of each step is of critical importance to understand how to control tracer accumulation in $sst_2$ expressing tumor cells. Thus, the objective of this study was to examine the effect of glycation on the internalization and recycling kinetics of radiolabelled octreotide and octreotate analogues.

$Tyr^3$-octreotide (TOC), $Tyr^3$-octreotate (TOCA) and their respective glucose (Gluc), maltose (Malt) and maltotriose (Mtr) derivatives were synthesized via Fmoc-SPPS and subsequent carbohydrate conjugation. Radioiodination was performed using the iodogen method. Radiochemical yields ranged from 50 to 84% after RP-HPLC-purification. Precursors for $^{99m}$Tc-labelling (Gluc-Lys$^0$(N$^\epsilon$-His)TOC(Gluc-K(H)-TOC) and Mtr-Lys$^0$(N$^\epsilon$-His)TOC(Mtr-K(H)-TOC)) were prepared analogously to the peptides mentioned above. Labelling with $^{99m}$Tc was carried out according to the $[[^{99m}Tc] (CO)_3(H_2O)_3]^+$ aquaion protocol previously described (Egli A. et al. *J. Nucl. Med.* 40: 1913-1917 (1999)). For comparison, we also included [$^{111}$In]Octreoscan and [$^{111}$In]DOTATOC into our study.

Internalisation and externalisation experiments were performed using the $sst_2$ expressing rat pancreatic tumor cell line AR42J. Free, surface bound and internalised radioactivity were determined after 10, 30, 60, 90 and 120 min. of incubation with the radioligands at 37° C. In the externalisation experiments allowing ligand recycling, the fraction of radioactivity released into the supernatant during 10, 30, 60, 90 and 120 min as well as the radioactivity remaining in the cells were determined. We also measured the activity released during 5 subsequent incubations (10, 20 and 3×30 min) with intermediate changes of the medium (limited recycling).

The influence of carbohydration of TOC on the internalization parallels the size of the sugar used. Compared to [$^{125}$I]TOC only the glucose conjugate showed enhanced uptake in the cells. In contrast, intracellular accumulation of both [$^{125}$I]Gluc-TOCA and [$^{125}$I]Mtr-TOCA (Table 2) was significantly increased (7.36±0.50 and 5.68±0.38 fold compared to [$^{125}$I]TOC). Comparing the internalisation characteristics of TOC and TOCA and of the respective glucosylated derivatives, we observed a synergistic effect of both structural modifications (substitution of Thr(ol)$^8$ by Thr$^8$ and carbohydration) on surface availability and on internalisation rate.

Compared to [$^{111}$In]Octreoscan and [$^{111}$In]DOTATOC, the internalization of both $^{99m}$Tc-labelled carbohydrated derivatives was unexpectedly high.

Pretreatment experiments with 10 µM sandostatin reduced the ligand uptake to a max. of 5% of control, indicating i) $sst_2$ specific uptake and ii) that no carbohydrate related uptake mechanism is involved (Table 2). For all tracers investigated, the internalized activity strongly correlates with the surface availability of the ligands.

TABLE 2

Internalisation data obtained after a 60 min incubation with AR42J cells Internalisation values as well as ratios are normalized to the reference [$^{125}$I]TOC

|  | internalised ligand | surface availability$^a$ | internalisation rate$^b$ |
|---|---|---|---|
| [$^{125}$I]Mtr-TOC | 42 ± 7* | 47 ± 11 | 87 ± 8 |
| [$^{125}$I]Malt-TOC | 66 ± 4 | 68 ± 11 | 95 ± 18 |
| [$^{125}$I]TOC | 100 | 100 | 100 |
| [$^{125}$I]Gluc-TOC | 143 ± 14 | 136 ± 13 | 110 ± 12 |
| [$^{125}$I]TOCA | 204 ± 7* | 182 ± 6 | 140 ± 8 |
| [$^{125}$I]Gluc-TOCA | 736 ± 50* | 583 ± 53 | 196 ± 21 |
| [$^{125}$I]Mtr-TOCA | 568 ± 38* | 312 ± 25 | 216 ± 26 |
| [$^{111}$In]Octreoscan | 16 ± 2 | 24 ± 2 | 63 ± 12 |
| [$^{111}$In]DOTATOC | 30 ± 7 | 28 ± 7 | 55 ± 11 |
| [$^{99m}$Tc]Gluc-K$^0$(H)-TOC | 234 ± 24 | 204 ± 54 | 171 ± 29 |
| [$^{99m}$Tc]Mtr-K$^0$(H)-TOC | 298 ± 37 | 195 ± 35 | 186 ± 14 |

$^a$surface availability = % surface-bound ligand/% free radioligand
$^b$internalisation rate = % internalised ligand/% surface-bound ligand
*pre-treatment experiments with 10 M sandostatin reduced cellular ligand uptake by a minimum of 95%

With respect to externalisation glycosylation seems to have no influence. The degree of externalisation of radioligand from the cells is primarily determined by the nature of the peptide (TOC or TOCA) and also by the intracellular fate of the label. In the externalisation experiment that allowed ligand recycling, TOCA and its glycated derivatives showed about of extracellularly located radioactivity compared to the experiment without recycling, while about 80% were found for TOC, Gluc-TOC and Mtr-TOC. [$^{99m}$Tc]Gluc-K$^0$(H)-TOC as well as both $^{111}$In-labelled compounds showed nearly quantitative retention in the cell within 120 min under recycling conditions. In contrast, intracellular activity of [$^{111}$In] Octreoscan and [$^{111}$In]DOTATOC was depleted by 33% and 49% during 120 min, when recycling was limited.

Example 4

[Tc-99 m](CO)$_3$-Labeled Carbohydrated SSTR-Ligands: Synthesis, Internalization Kinetics and Biodistribution on a Rat Pancreatic Tumor Model Aim:

This study is to demonstrate the design of tracers for specific and high-level targeting of SSTR expressing tumors. For this purpose we introduced carbohydrated octreotide derivatives to optimize pharmacokinetics and to improve SSTR specific internalization and tumor retention. Here we describe compounds of a series of new carbohydrated $^{99m}$Tc-SSTR ligands.

Methods:

Coupling of glucose (Gluc) and maltotriose (Mtr) to N$^\alpha$-Lys of N$^\epsilon$-(Boc-His(Boc))Lys$^0$-Tyr$^3$-Lys$^5$(Dde)-octreotide (protected K(H)TOC) and final deprotection yielded Gluc- and Mtr-K(H)TOC. $^{99m}$Tc-labeling was carried out using [$^{99m}$Tc(H$_2$O)$_3$(CO)$_3$]$^+$. Internalization and externalization studies (<2 h) were performed using the SSTR$_2$ expressing rat pancreatic cell line AR42J and [$^{125}$I]Tyr$^3$-octreotide ([$^{125}$I] TOC) as a reference. Biodistribution was evaluated in nude mice bearing AR42J tumors at 0.5 and 2 h p.i (n=4).

Results:

Radiolabeling produced efficiently (0.5 h, RCY>97%) uniform products. Compared to [$^{125}$I]TOC, both carbohydrated peptides showed significantly higher intercellular activity levels; e.g. at 2 h 2.3±0.2 times higher levels for [$^{99m}$Tc]Gluc-K(H)TOC and 3.6±0.4 times higher levels for [$^{99m}$Tc]Mtr-K(H)TOC. Externalization studies revealed a decrease of about 50% of intracellular activity for [$^{125}$I]TOC within 2 h, while the intercellular level of [$^{99m}$Tc]Gluc-K(H)TOC was almost stable up to 2 h, demonstrating retention of this tracer. In vivo, tumor accumulation reached 12.2±1.0 and 14.0±6.3% ID/g at 2 h p.i. with blood levels of 1.5±0.2% ID/g and 4.4±1.0% ID/g for [$^{99m}$Tc]Gluc-K(H)TOC(T/liver 0.77, T/kidney 0.63) and [$^{99m}$Tc]Mtr-K(H)TOC (T/liver 0.97, T/kidney 0.84), respectively.

Conclusion:

These results demonstrate the usefulness of carbohydration as a tool to improve SSTR targeting.

Example 5

[Tc-99 m](CO)$_3$-Labeled Carbohydrated SSTR-Ligands: Synthesis, Internalization Kinetics and Biodistribution on a Rat Pancreatic Tumor Model Aim:

This study is part of our endeavor to design tracers for specific and high-level targeting of SSTR expressing tumors. For this purpose we use suitable carbohydrate moieties to optimize the pharmacokinetics and to improve SSTR specific internalization and tumor retention. Here we describe for the first time carbohydrated SSTR binding peptides labeled via the [$^{99m}$Tc (H$_2$O)$_3$ (CO)$_3$]$^+$ aquaion approach.

Methods:

N$^\epsilon$(Boc-His(Boc))Lys$^0$-Tyr$^3$-Lys$^5$ (Dde)-octreotide (protected K(H)TOC) was synthesized using standard Fmoc-chemistry. Coupling of glucose (Gluc) and maltotriose (Mtr) to N$^\alpha$-Lys$^0$ and final deprotection yielded the Gluc- and Mtr-derivatives of K(H)TOC. Tc-99m-labeling was carried out using the organometallic aquaion [$^{99m}$Tc (H$_2$O)$_3$ (CO)$_3$]$^+$(1). Internalization and externalization studies (<120 min) were performed for both compounds using the SSTR$_2$ expressing cell line AR42J. For the in vitro studies [$^{125}$I]Tyr$^3$-octreotide ([$^{125}$I]TOC) was used as a reference. Biodistribution of intravenously administered [$^{99m}$Tc]Gluc-K(H)TOC and [$^{99m}$Tc]Mtr-K(H)TOC was evaluated in nude mice bearing AR42J rat pancreatic tumors at 30 and 120 min p.i.(n=4).

Results:

The labeling procedure produced efficiently (30 min, RCY>97%) uniform products (LHPLC). Compared to the reference [$^{125}$I]TOC, both carbohydrated peptides were significantly higher internalized at all time points investigated; e.g. at 120 min 2.3±0.2 times higher levels for [$^{99m}$Tc]Gluc-K(H)TOC and 3.6±0.4 times higher levels for [$^{99m}$Tc]Gluc-K(H)TOC and 3.6±0.4 times higher levels for [$^{99m}$Tc]Mtr-K(H)TOC. Furthermore, externalization studies revealed a decrease of about 50% of intracellular activity for the reference compound within 120 min, while the high level of intracellular [$^{99m}$Tc]Gluc-K(H)TOC was almost stable up to 2h, demonstrating retention of this tracer in the cell line investigated. In vivo, tumor accumulation reached 12.2±1.0 and 14.0±6.3% ID/g at 120 min p.i. with corresponding blood activity levels of 1.5±0.2% ID/g and 4.4±11.0% ID/g for [$^{99m}$Tc]Gluc-K(H)TOC (T/liver 0.77, T/kidney 0.63) and [$^{99m}$Tc]Mtr-K(H)TOC(T/liver 0.97, T/kidney 0.84), respectively.

Conclusion:

These results demonstrate the usefulness of carbohydration as a tool to improve SSTR targeting.

Example 6

Solid Phase Peptide Synthesis

1. Fmoc-Lys$^0$-Tyr$^3$-Lys(Dde)$^5$-octreotide (Fmoc-Lys$^0$-TOC (Dde)) Fmoc-Thr (tBu)-ol A solution of Fmoc-Thr(tBu)-OH (1.391 g, 3.5 mmol) in 30 ml of tetrahydrofurane (THF) was cooled to −10° C. N-methylmorpholine (386 ul, 3.5 mmol) and ethylchloroformate (333 ul, 3.5 mmol) were added successively. The reaction mixture was stirred at −10° C. for 30 min. Then sodium borohydride (396 mg, 10.5 mmol) was added. Over a period of 30 min 60 ml of methanol were slowly added to the reaction mixture, which was then stirred at 0° C. for 3 hours.

After the addition of 50-70 ml of 1 N HCl (the cloudy reaction mixture has to become transparent) the organic solvents were evaporated and the remaining aqueous phase was extracted twice with dichloromethane (DCM). Extraction efficiency was monitored by thin layer chromatography (product R$_f$=0.83 in ethyl acetate (AcOEt)) of both phases. The combined organic layers were dried over magnesium sulfate, filtered and concentrated in vacuo to yield a yellowish oil. The crude product was purified by flash chromatography using AcOEt. The product was obtained as an oil (1.19 g, 89%).

Calculated monoisotopic mass for C$_{23}$H$_{29}$NO$_4$=383.21; found: m/z=406.1[M=Na]$^+$.

SPPS of Fmoc-Lys$^0$-Dphe$^1$-Cys$^2$-Tyr$^3$-DTrp$^4$-Lys (Dde) 5-Thr$^6$-Cys$^7$-Thr-ol$^8$ DHP-HM(3,4-Dihydro-2H-Pyran-2-ylmethoxymethylpolystyrol)-resin (1.000 g, 0.94 mmol/g) was allowed to preswell in 10 ml of dry DCE (1,2-Dichloroethane) for 1 hour. Then a solution of Fmoc-Thr(tBu)-ol (1.266 g, 3.3 mmol) and of Pyridinium-p-toluenesulfonate (414 mg, 1.75 mmol) in 7 ml of dry DCE was added and the reaction mixture was stirred overnight at 80° C. under argon. To cap free functional groups on the resin 5 ml of pyridine were added and the suspension was stirred for another 15 min at room temperature. The loaded resin was then filtered off, washed twice with DMF (N,N-Dimethylformamide) and with DCM and dried in an exsiccator. Final load of the resin was 0.834 mmol/g. The peptide sequence was assembled on the resin bound amino alcohol using standard Fmoc-protocol. Briefly, the N-terminal Fmoc was removed with 20% piperidine in DMF, and the resin of resin-supported peptide was washed with NMP (N-Methylpyrrolidone). Coupling was carried out in NMP by reacting 1.5 eq of amino acid derivative with 1.5 eq of HOBt (1-Hydroxybenzotriazol), 1.5 eq of TBTU (O-(1H-benzoltriazol-1-yl)-N,N,N',N'-Tetramethyluronium-Tetrafluoroborate) and 3.5 eq of DIPEA (N-Ethyl-diisopropylamine). After adding the activated amino acid to the reaction vessel, the resin was agitated for an appropriate amount of time (usually 40-60 min). The resin was then washed with additional NMP. The sequence of addition for the synthesis of TOC was Fmoc-Cys(Trt), Fmoc-Thr(tBu), Fmoc-Lys(Dde), Fmoc-DTrp, Fmoc-Tyr, Fmoc-Cys(Trt), Fmoc-Dphe and Fmoc-Lys(Boc). After the coupling of the last amino acid to the sequence, the resin was washed several times with NMP and DCM. Cleavage from the resin and deprotection of the Thr-, Cys- and Lys$^0$-sidechains was performed using a mixture of TFA (trifluoroacetic acid)/TIBS (triisobutylsilane)/water (95:2.5:2.5) and DCM (1:1). After 90 min the resin was filtered and washed twice with DCM. The combined filtrates were concentrated using a rotary evaporator and the crude product was precipitated with ether. We obtained 828 mg of crude produce. Yield: 83%

The crude peptide was resuspended in 50 ml of THF (per 300 mg of peptide), and 5 mM ammonium acetate was added, until a clear solution was obtained. The pH was adjusted to 7 by dropwise addition of a saturated solution of $NaHCO_3$. Then 100 ul (per 300 mg of peptide) of hydrogen peroxide (30%) were added. After 30 min of stirring at room temperature cyclisation was complete (gradient HPLC-control: 30-80% B in 15 min). The solvents were evaporated, and the cyclised product was lyophilized. Yields were quantitative.

Calculated monoisotopic mass for $C_{80}H_{100}N_{12}O_{16}S_2=1548.68$; found: m/z=1549.5 $[M+H]^+$, m/z=1571.5 $[M+Na]^+$.

2. Fmoc-$Lys^0$-$Tyr^3$-Lys (Dde) 5-octreotide (Fmoc-$Lys^0$-TATE (Dde)) Fmoc-$Lys^0$-$Dphe^1$-$Cys^2$-$Tyr^3$-$DTrp^4$-Lys $(Dde)^5$-$Thr^6$-$Cys^7$-$Thr^8$ To 1.502 g of dry TCP-resin a solution of 894 mg (2.25 mmol) of Fmoc-Thr(tBu) and 321 ul (1.87 mmol) of DIPEA in 15 ml of dry DCM was added. After stirring for 5 min, another 642 up (3.76 mmol) of DIPEA were added. After vigorous stirring for 90 min at room temperature, 1.5 ml of methanol were added to cap unreacted Tritylchloride groups. After 15 min the resin was filtered, washed twice with DCM, DMF and methanol respectively and dried in vacuo. Final load of the resin was 0.77 mmol/g. Synthesis of the peptide sequence Cys(Trt)-Thr(tBu)-Lys(Dde)-DTrp-Tyr-Cys(Trt)-Dphe-Lys(Boc)-Fmoc on the resin-bound amino acid, deprotection and cleavage from the resin as well as cyclisation were performed as described for Fmoc-$Lys^0$-TOC(Dde).

Calculated monoisotopic mass for $C_{80}H_{98}N_{12}O_{17}S_2=1562.66$; found: m/z=$([M+H]^+)$ Solution Phase Derivatization
$Lys0(N_\epsilon$-Boc-His (Boc))-TOC(Dde)

A solution of 500 mg (0.32 mmol) of Fmoc-$Lys^0$-TOC (Dde), 170 mg (0.48 mmol) of Boc-His(Boc), 65 mg (0.048 mmol) of HOBt, 154 mg (0.48 mmol) of TBTU and 300 ul (1.75 mmol) of DIPEA in 3 ml of DMF was stirred at room temperature. RP-HPLC analysis (gradient: 30-80% B in 15 main) revealed that the reaction was complete within 30 min. The product was precipitated using water and dried in vacuo. To remove the N-terminal Fmoc-protecting group, the peptide was dissolved in 1 ml piperidine/DMF (1:4) and stirred for 15 min. Precipitation with ether afforded the deprotected product with a yield of 86%.

Calculated monoisotopic mass for $C_{81}H_{113}N_{15}O_{19}S_2=1663.78$; found: m/z=1873.6 $[M+H]^+$, m/z=1895.7 $[M+Na]^+$.

$Lys^0$-$N_a$-Amadori Derivatives of $Lys^0$(Boo-His(Boc))-TOC (Dde)

Based on a method reported previously[1], 1 equiv. of $Lys^0$-(Boc-His(Boc))-TOC(Dde) and 10 equiv. of the respective aldose (Glucose=S1, Maltose=S2, Maltotriose=S3) were dissolved in methanol/acetic acid (95:5), and the reaction mixture was stirred at 60° C. for 24-48 h. The solvents were then evaporated, and the crude product was precipitated by the addition of ether.

To remove the Dde-protection group, the glycosylated peptide was redissolved in a small volume of DMF, 2 vol % of hydrazine hydrate were added and the solution was stirred at room temperature for 15 min. The deprotected peptide was precipitated by the addition of ether, washed with ether and dried in vacuo. Boc-protecting groups on the His-residue were then removed redissolving the crude products in a small volume of TFA/TIBS/water (95:2.5:2.5) and stirring for 15 min at room temperature. The products were precipitated using either and purified via preparative RP-HPLC (gradient: 10-60% B in 30 min). Yields ranged from 17-32%.

S1-$Lys^0$(His)TOC($N_a$ -(1-deoxy-D-fructosyl)-$Lys^0$N$\epsilon$-His)-$Tyr^3$-octreotide):

Calculated monoisotopic mass for $C_{67}H_{95}N_{15}O_{18}S_2=1461.60$; found: m/s ~1873.6 $[M+H]^+$, m/z=1895.7 $[M+Na]^+$.

S2-$Lys^0$(His)TOC($N_a$ -(O-    -D-glucopyranosyl-(1-4)-1-deoxy-D-fructosyl)-$Lys^0$($N_\epsilon$-His)-Tyr3-octreotide):

Calculated monoisotopic mass for $C_{73}H_{105}N_{15}O_{23}S_2=1623.70$; found: m/z=1873.6 $[M+H]^+$, m/z=1895.7 $[M+Na]^+$.

S3-$Lys^0$(His) TOC($N_a$ -(O$^-_a$ -D-glucopyranosyl-(1-4)-O-$_a$ -D-glucopyranousyl-(1-4)-1-deoxy-D-fructosyl)-$Lys^0$ (N$\epsilon$-His)-Tyr3-octreotide:

Calculated monoisotopic-mass for $C_{79}H_{115}N_{15}O^{28}S^2=1785.75$; found: m/z=1873.6 $[M+H]^+$, m/z −1895.7 $[M+Na]^+$.

3. $Lys^0$(N$\epsilon$-2-picolylamino-. . . )TATE(Dde) 2-Picolylamine N,N-diacetic $acid^2$ Imino diacetic acid (3.25 g, 24.4 mmol) was dissolved in a mixture of 30 ml of absolute ethanol and a solution of 1.95 g of NaOH (49 mmol) in 10 ml of water. After the addition of 4.00 g of picolylchloride (24.4 mmol) in 9 ml of water and of 1.95 g of NaOH (49 mmol) in 4 ml of water, the solution was stirred at 70° C. for 2 h. Then another 1.95 g (49 mmol) of NaOH were added and the solution was stirred for another 1.5 h at 70° C. TLC reaction control (AcOEt) revealed complete disappearance of the reactants at that time. The solvents were evaporated in vacuo, and the residue was redissolved in 25 ml of water. After adjusting the pH of the solution to 1.5 with concentrated hydrochloric acid, the solution was again evaporated to dryness. By several successive steps of resuspension of the residue with methanol under reflex, hot filtration of the suspension and concentration of the filtrate in vacuo, excess NaCl was successfully removed. The picolylamino diacetic acid crystallized from the remaining methanolic solution overnight at −20° C.

Calculated monoisotopic mass for $C_{10}H_{12}N_2O_4=224.08$; found: m/z=[M=H]+(disodium salt).

Coupling of 2-picolylamine N,N-diacetic acid to Fmoc-$Lys^0$-TATE (Dde)

A solution of 52 mg (0.19 mmol) of 2-picolylamine N,N-diacetic acid, 26 mg (0.19 mmol) of HOBt, 62 mg (0.19 mmol) of TBTU and 176 µl (1.75 mmol) of DIPEA in 2 ml of DMF was stirred at room temperature for 10 min. This solution was added dropwise to a solution of 200 mg (0.13 mmol) of Fmoc-$Lys^0$-TATE(Dde) in 1 ml of DMF under vigorous stirring. After 30 min the product was precipitated using diethyl either and dried in vacuo. To remove the N-terminal Fmoc-protecting group, the peptide was dissolved in 2 ml piperidine/DMF (1:4) and stirred for 10 min. Precipitation with ether afforded the deprotected product with a yield of 84%.

Calculated monoisotopic mass for $C_{75}H_{98}N_{14}O_{18}S_2=1546.66$; found: m/z=$[M=H]^+$, m/z=$[M+Na]^+$.

$Lys^0$-$N_a$-Amadori Derivatives of $Lys^0$(Pic)TATE(Dde)

Conjugation of $Lys^0$(Pic)TATE(Dde) with glucose and subsequent Dde-deprotection were carried out as described for the $Lys^0$-$N_a$-Amadori derivatives of $Lys^0$(Boc-His (Boc))-TOC(Dde)

Calculated monoisotopic mass for $C_{71}H_{96}N_{14}O_{21}S_2=1544.63$; found: m/z=$[M=H]^+$, m/z=$[M+Na]^+$.

Radiolabelling

Based on the organometallic aquaion $[^{99m}Tc(H_2O)_3(CO)_3]^+$-method reported recently[3], 10 mg of $NaBH_4$, 8 mg of $Na_2CO_3$ and 41.5 mg of Na/K tartrate were dissolved in 600 μl of [$^{99m}$Tc]pertechnetate eluate in a glass flask. The flask was then connected to a CO-filled balloon and sealed tightly. After stirring at 75° C. for 45 min, the solution was cooled on an ice bath and 150 μl of phosphate buffered saline (PBS, pH-7.4) were added. To destroy the reducing agent, 600 μl of 1 N HCl were added. Then the solution was neutralized with 500 μl of a saturated solution of $NaHCO_3$. The presence of the $[^{99m}Tc(H_2O)_3(CO)_3]^+$-aquaion was confirmed via TLC (5% conc. HCl in methanol).

After adding 1 ml of the $[^{99m}Tc(H_2O)_3(CO)_3]^+$-solution (51 MBq) to 700 μg of S1-Lys$^0$(His)TOC, the mixture was heated to 75° C. for 30 min. Gradient HPLC purification afforded the radiochemically pure peptide $N_a$-(1-deoxy-D-fructosyl)-
Lys$^0$($N_\epsilon$-His $[^{99m}Tc (H_2O)(CO)_3]+$)-Tyr$^3$-octreotide with a radiochemical yield of 34%.

S3-Lys$^0$(His)TOC was labelled in an analogous manner.

Determination of Lipophilicity

To a solution of app. 300000 cpm of radiolabeled peptide in 500 ml of PBS (pH 7.4), 500 ml of octanol were added (n=6). Vials were vortexed for 3 min and then centrifuged at 15000 rpm for 6 min. Aliquots of 100 ml of PBS and octanol were measured in a γ-Counter.

| | |
|---|---|
| S1-Lys$^0$(His)TOC: | log Pow = −0.673 ± 0.064 |
| S3-Lys$^0$(His)TOC: | log Pow = −1.304 ± 0.040 |

In Vitro Experiments

AR42J cells were maintained in RPMI 1640, supplemented with 10% FCS and 2 mM L-glutamine.

Internalization Studies

Six-well plates with a cell population of $8\times10^5$-$5\times10^6$ AR42J-cells per well were incubated at 37° C. with fresh culture medium (RPMI 1640, 1% BSA, 2 mM L-glutamine) for 1 h prior to the experiment. Then app. 300000 cpm of radiometallated peptide in 10 μl of culture medium were added to each well (triplicate experiments for the reference compound (internal standard) [$^{125}$I]TOC and for the radiometallated compound of interest each). After incubating for 10, 30, 60, 90 or 120 min. at 37° C. the supernatant was collected and the cells were washed once with 1 ml of cold medium. The supernatant was pooled with the supernatant of the previous step. To remove receptor bound (acid releasable) radioactivity the cells were incubated at 37° C. with 1 ml of 0.02 M NaOAc (acid wash). After 10 min. the supernatant was collected, the cells were washed once with 1 ml of 0.02 M NaOAc and the supernatant was again pooled with the supernatant of the previous step. Then the cells were extracted with 1 ml of 1 N NaOH and the wells were rinsed once with PBS. This pooled fraction represents internalized radioligand. The activity in the NaOH-fraction as well as in the supernatant- and in the acid wash-fractions was counted in a γ-Counter.

Externalization Studies

As described for the internalization studies, the six-well plates were incubated at 37° C. with fresh culture medium (RPMI 1640, 1% BSA, 2 mM L-Glutamine) for 1H prior to the experiment. Then app. 300000 cpm of radiometallated peptide in 10 μl of culture medium were added to each well (triplicate experiments for the reference compound (internal standard) [125I]TOC and for the radiometallated compound of interest each). After incubating for 120 min. at 37° C., the supernatant was collected and the cells were washed once with 1 ml of cold medium. The supernatant was pooled with the supernatant of the previous step. To collect externalized radioactivity the cells were then incubated at 37° C. with 1 ml of culture medium. After 10, 30, 60, 90 and 120 minutes respectively, the supernatant was collected, the cells were washed once with 1 ml of culture medium and the supernatant was again pooled with the supernatant of the previous step. Then the cells were extracted with 1 ml of 1 N NaOH and the wells were rinsed once with PBS. This pooled fraction represents radioligand still located in the cell. The activity in the NaOH-fraction as well as in the supernatant- and in the externalisation-fractions was counted in a γ-Counter.

Externalization Studies without Recycling of the Tracer

As described for the previous experiment, a six-well plate was incubated for 120 min. at 37° C. with radioligand. The supernatant was collected and the cells were washed once with 1 ml of cold medium. The supernatant was pooled with the supernatant of the previous step. To collect externalized radioactivity the cells were then incubated at 37° C. with 1 ml of culture medium. After 10 min. the supernatant was collected and the cells were again incubated with 1 ml of culture medium for another 20 min. at 37° C. The supernatant was collected and the cells were three more times incubated with 1 ml of culture medium for 30 min. at 37° C. Then the cells were extracted with 1 ml of 1 N NaOH and the wells were rinsed once with PBS. This pooled fraction represents radioligand still located in the cell. The activity in the NaOH-fraction as well as in the externalisation-fractions at all time points was counted in a 7-Counter.

Biodistribution Studies

To establish tumor growth, subconfluent monolayer cells were treated with 1 mM EDTA, suspended, centrifuged and resuspended in RPMI 1640.

Nude mice (male and female, 6-8 weeks) were inoculated s.c. in the flank with $2.5\text{-}3\times10^7$ cells suspended in 100 μl of PBS (pH 7.4), were injected i.v. into the tail vein of nude mice bearing an AR42J tumor. The animals (n=3-4) were sacrificed 30 and 120 min p.i, and the organs of interest were dissected. The radioactivity was measured in weighted tissue samples using a gamma counter. Data are expressed in % iD/g tissue (mean±DS, n=3-4).

What is claimed is:

1. A somatostatin receptor (sst) binding molecule comprising:
   a peptidic ligand selected from the group consisting of octreotide and octreotate;
   a sugar selected from the group consisting of glucose, galactose, maltose, mannose, maltotriose, and lactose; and
   a multidentate chelating group selected from the group consisting of histidine, picolylamine diacetic acid, hydroxyl nicotine amide (HYNIC) and mercaptoacetyl-glycyl-glycine (MAG-3) that complexes a radioisotope selected from Tc and Re,
   wherein (i) the chelating group is bound to the N-terminal of the ligand and the sugar is bound to the chelating group or (ii) the sugar is bound to the N-terminal of the ligand and the chelating group is bound to the sugar.

2. The molecule of claim 1, wherein the radioisotope is an isotope of Tc.

3. The molecule of claim 1, wherein the chelating group is bound to the N-terminal of the ligand and the sugar is bound to the chelating group.

4. The molecule of claim 1, wherein the sugar is bound to the N-terminal of the ligand and the chelating group is bound to the sugar.

5. The molecule of claim 1, wherein the sugar is bound to the ligand or to the chelating group via a glycosidic bond.

6. The molecule of claim 4, wherein the sugar is a coupling product between an amino group of the ligand and the sugar via Amadori Reaction.

7. A pharmaceutical composition comprising the molecule of claim 1 and a pharmaceutically acceptable carrier.

8. A method of sst-imaging comprising administering to a patient in need thereof the composition of claim 7.

* * * * *